(12) United States Patent
Negre et al.

(10) Patent No.: US 8,630,695 B2
(45) Date of Patent: Jan. 14, 2014

(54) LOCATOR, DEVICE AND METHOD FOR ELECTRONICALLY LOCATING AND READING THE SETTING OF AN ADJUSTABLE VALVE

(75) Inventors: Philippe Negre, Paris (FR); Christophe Boyer, Miserey Salines (FR); Sylvain Morel, Pontarlier (FR); Christophe Moureaux, Bensançon (FR)

(73) Assignee: Sophysa, Orsay Cedex (FR)

( * ) Notice: Subject to any disclaimer, the term of this patent is extended or adjusted under 35 U.S.C. 154(b) by 306 days.

(21) Appl. No.: 12/747,630

(22) PCT Filed: Dec. 14, 2007
(Under 37 CFR 1.47)

(86) PCT No.: PCT/IB2007/004438
§ 371 (c)(1),
(2), (4) Date: Feb. 3, 2011

(87) PCT Pub. No.: WO2009/077811
PCT Pub. Date: Jun. 25, 2009

(65) Prior Publication Data
US 2011/0118589 A1  May 19, 2011

(51) Int. Cl.
*A61B 5/05* (2006.01)
*A61B 19/00* (2006.01)
(52) U.S. Cl.
USPC .......................... 600/424; 600/409; 128/899

(58) Field of Classification Search
USPC .................................. 600/409, 424; 128/899
See application file for complete search history.

(56) References Cited

U.S. PATENT DOCUMENTS

| 5,758,667 | A | * | 6/1998 | Slettenmark | 128/899 |
|---|---|---|---|---|---|
| 5,879,297 | A | * | 3/1999 | Haynor et al. | 600/407 |
| 6,129,668 | A | * | 10/2000 | Haynor et al. | 600/424 |
| 7,508,202 | B2 | * | 3/2009 | Tilbrook | 324/248 |
| 2005/0092335 | A1 | * | 5/2005 | Bertrand et al. | 128/899 |

FOREIGN PATENT DOCUMENTS

EP          1 092 450          4/2001

* cited by examiner

*Primary Examiner* — Long V. Le
*Assistant Examiner* — Katherine Fernandez
(74) *Attorney, Agent, or Firm* — Clark & Brody

(57) ABSTRACT

The invention is aimed at improving valve pinpointing and reading devices by proposing to activate a magnetic detection source allowing measurements regularly-distributed in a circle around an axis at predetermined measurement positions. An exemplary locator comprises a casing (26) provided with a mechanism for detecting and analyzing the magnetic field of the magnetic dipole of the valve. It comprises:—a magnetic detection source (36) able to detect and measure the magnetic field of the magnetic center of the valve at predetermined measurement positions distributed in a circle around an axis (X-X'), linked to—a microprocessor (32) for analyzing the measurements and for generating detection signals.

25 Claims, 9 Drawing Sheets

Figure 1:
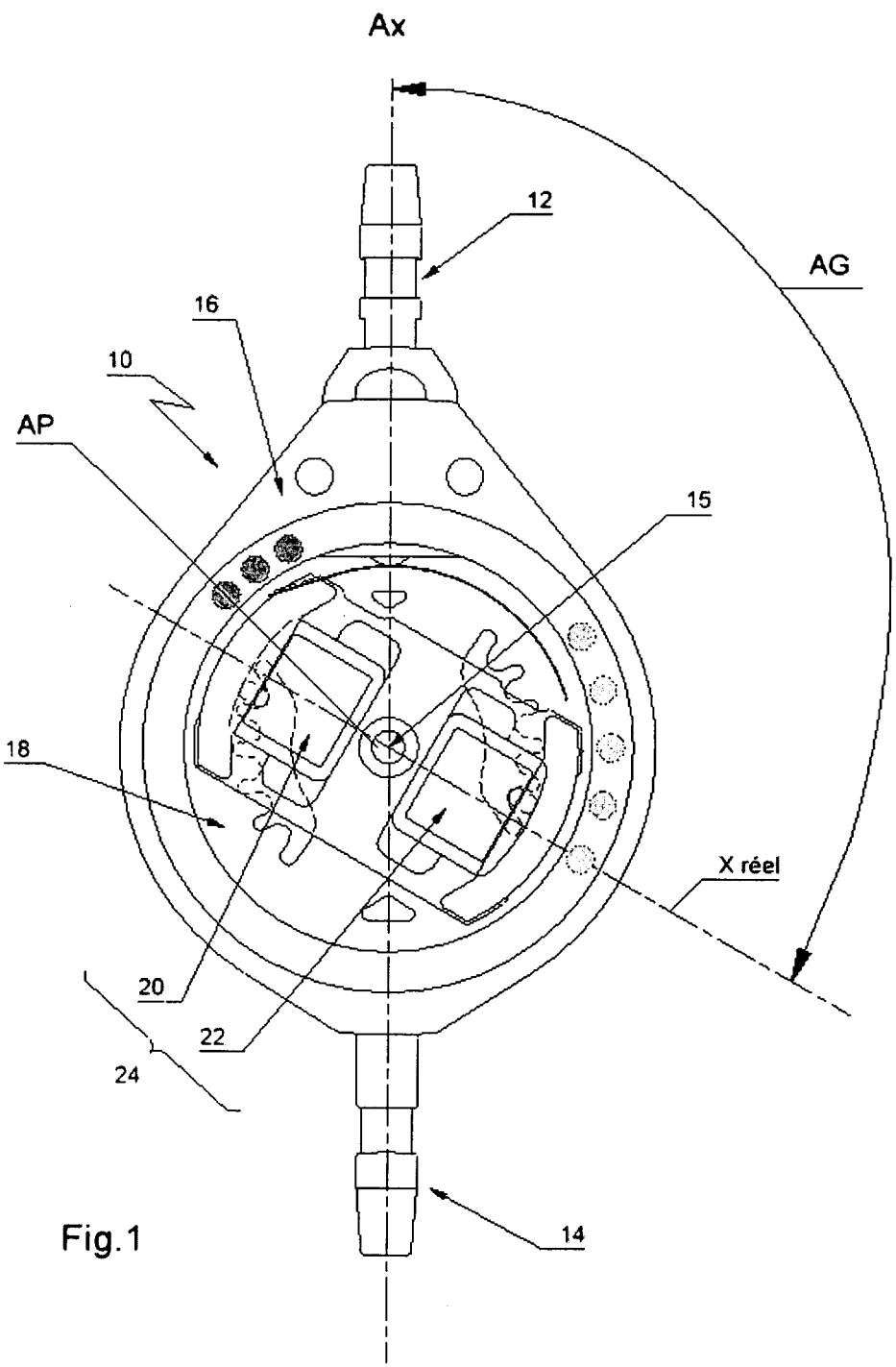

LOCATOR, DEVICE AND METHOD FOR ELECTRONICALLY LOCATING AND READING THE SETTING OF AN ADJUSTABLE VALVE

The present invention relates to a method and device for electronically locating a subcutaneous adjustable valve, of adjustable neurological valve type using a magnetic dipole rotor, and for accurately detecting its magnetic centre and the orientation of its dipole so as to determine and display its pressure setting.

A valve of this type is used for the treatment of hydrocephalus and consists, for example, of an adjustable pressure valve which allows fluid flow beyond a determined pressure setting.

It is known to indicate the orientation of the field created by the magnetic rotor of the valve, generally formed by two magnets, with a compass. Such a compass lacks accuracy both in the centring of the compass on the magnetic centre and in its liberation from terrestrial or external magnetic fields.

Electronic devices have also been developed, such as those described in patent documents U.S. Pat. No. 5,879,297 and U.S. Pat. No. 6,129,668. These devices are of complex structures since they comprise four groups of sensors, the latter being disposed in three dimensions inside each group. This necessitates a first processing within the groups of sensors, followed by a processing to locate the centre of the valve.

The invention is aimed at overcoming these drawbacks by proposing a pinpointing of the magnetic centre of the valve, or even a reading of the pressure setting, by using a simple and efficient arrangement of the detection means.

More precisely, the subject of the present invention is a method for locating an implanted magnetic valve exhibiting a fluid flow axis and a centre furnished with a magnetic dipole, said method consisting in pinpointing the magnetic centre of the valve, after a preliminary phase of pinpointing the reference axis for the flow of the fluid through the valve. The method comprises the following steps:

activating a magnetic detection source allowing measurements regularly distributed in a circle around an axis at predetermined measurement positions, measuring the magnetic field emitted by the valve at the predetermined measurement positions, displacing the magnetic detection source until the magnetic field measured is substantially the same, whatever the sign is, at substantially diametrically opposite positions (i.e. until the absolute values are substantially the same).

According to preferred embodiments:

the method can comprise, furthermore, the step consisting in pinpointing the orientation of the dipole of the valve with respect to the flow axis on the basis of the magnetic field measurements;

the orientation of the dipole may be pinpointed by implementing the following steps:

a) searching for the measurement position having the strongest negative signal;

b) searching, on the basis of the position determined in step a) and according to the direction of rotation, among the subsequent positions of the sensor, for the position having the strongest positive signal;

c) searching for the position Imin1 of the sensor having the weakest signal in terms of absolute value situated between the two positions determined in steps a) and b);

d) determining, from among the positions preceding and succeeding the position Imin1 determined in step c), the position Imin2 of the sensor having the weakest signal in terms of absolute value;

the setting position of the valve being equal to:

Imin1+Imin2, if Imin1 is less than Imin2, or to Imin1+Imin2+1, if Imin2 is less than Imin1;

the method can comprise, furthermore, the steps e) of calculating the depth of implantation of the valve on the basis of the mean of the absolute values of the measurements taken at each position, and f) of indicating the depth of the valve by comparing the mean obtained with predetermined calibration values;

the magnetic detection source may be rotated about said axis and in a determined direction of rotation, the measurements of the magnetic field emitted by the valve being made at the predetermined measurement positions;

the magnetic detection source may move in rotation at constant speed during the measurements;

the magnetic detection source may be associated with a magnetic field channelling means; and/or the magnetic detection source may comprise a plurality of sensors angularly distributed in a uniform manner at predetermined angular positions around an axis of symmetry, the measurements of the magnetic field emitted by the valve being made by each sensor of the source at the predetermined angular positions.

The invention also relates to a locator of the magnetic centre of an implanted valve for implementing the method above comprising a casing provided with a mechanism for detecting and analysing the magnetic field of the magnetic dipole of the valve. It comprises:

a magnetic detection source able to detect and measure the magnetic field of the magnetic centre of the valve at predetermined measurement positions distributed in a circle around an axis, linked to a microprocessor for analysing the measurements and for generating detection signals.

According to preferred embodiments:

a screen for displaying the position of the magnetic centre of the valve may be provided;

the magnetic detection source may be mounted rotatably about said axis and a direction of rotation;

the magnetic detection source may comprise at least one magnetic sensor for performing the measurements of magnetic field of the magnetic centre of the valve and a support able to be driven in rotation by a motor;

the mechanism for detecting and analysing the magnetic field of the magnetic dipole of the valve may comprise a motor devised so as to drive in rotation, according to said axis, a support comprising a first coil for supplying energy and transmitting information and a magnetic sensor, the first coil being associated with a second fixed coil to form an energy transponder for the sensor and to communicate the measurements and the data originating from the transponder to the microprocessor, a coded wheel being disposed between the motor and the support for ascertaining the exact angular position of the magnetic sensor during rotation;

the mechanism for detecting and analysing the magnetic field of the magnetic dipole of the valve may comprise a motor exhibiting a shaft for driving according to said axis, covered by a fixed hood on which is positioned a magnetic sensor, able to communicate with said microprocessor, and linked kinematically to a support by a coded wheel, the support exhibiting a doubly bent prolongation made of a magnetic material, in particular ferrite, whose position is determined by the coded wheel;

the mechanism for detecting and analysing the magnetic field of the magnetic dipole of the valve may comprise a motor kinematically linked to a support comprising a rotary central pin linked kinematically to the drive motor and an arm fixed to the central pin so as to be driven in rotation with the central pin, the arm being equipped with a magnetic sensor and with an information collecting coil associated with a second coil to form an energy transponder for the sensor and to communicate the measurements and the data of the sensor to the microprocessor;

the magnetic detection source may comprise a plurality of sensors angularly distributed in a uniform manner at predetermined measurement positions around the axis;

the detection signals generated by the microprocessor may be embodied by a visual signal on the screen or an audible signal;

the visual signal may be constant or vary as a function of the distance between the valve and the locator in such a way that the location of the magnetic centre of the valve is acquired when the disc is centred in the sight;

the locator may comprise an indicator for displaying the depth of the valve such as a bar graph, independent of the valve pinpointing signal;

light-emitting diodes may be disposed around a perimeter of the casing of the locator and are linked to the microprocessor for analysing the magnetic field measurements in such a way that, when the magnetic centre is located and the reference axes of the locator and of the valve previously aligned, the diode corresponding most closely to the orientation of the magnetic dipole of the valve lights up, and the pressure corresponding to this orientation can be read opposite the lit diode;

the locator may comprise a sound emitter able to emit a particular sound signal when the positions of the magnetic centre of the valve and of the sight of the locator are superimposed; and/or the magnetic sensor may be a magnetorestrictive, inductive, piezoelectric or Hall-effect sensor.

The invention also relates to a device for pinpointing and detecting valve pressure for implementing the method above, said device comprising two separable parts, namely a locator as described above and a selector of tubular structure exhibiting a collar intended to serve as seat for the locator, the collar comprising an alignment frame for aligning the selector with respect to the axis of flow of the fluid through the valve.

The device can comprise a locator as above, in which the collar carries indications of pressure values written in such a way as to be opposite the diodes of the locator when the selector and the locator are associated.

Figure 2A:
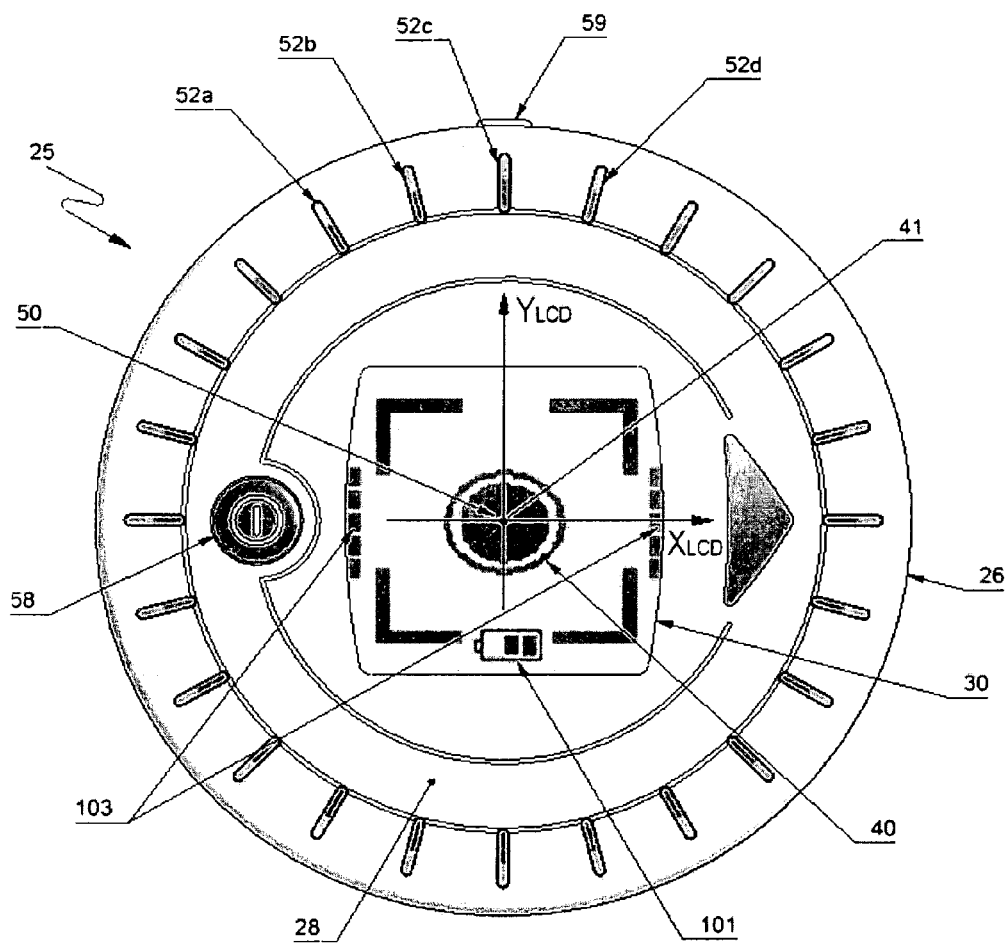
Figure 2B:
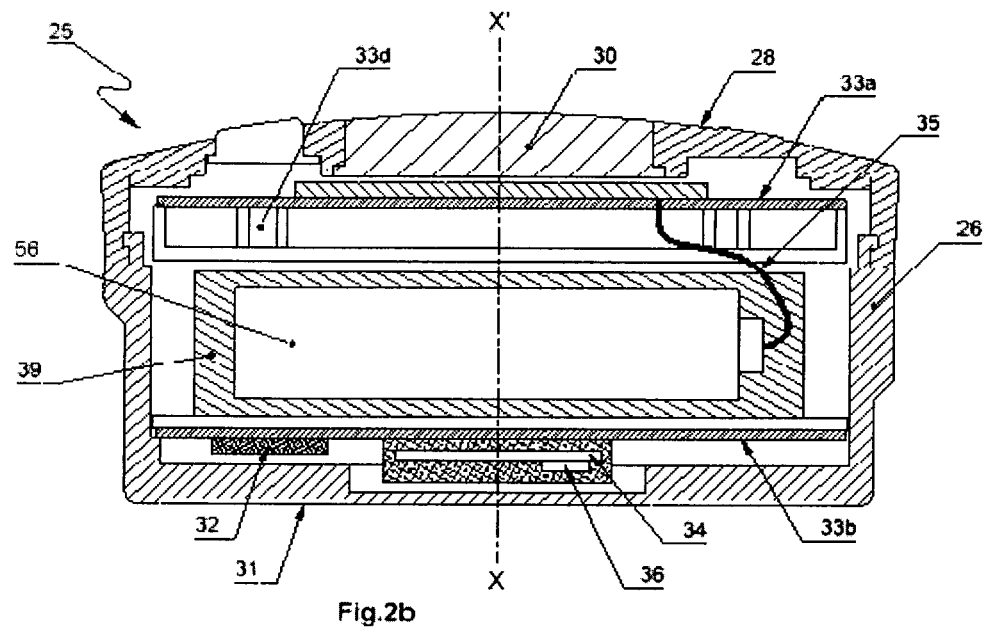
Figure 2C:
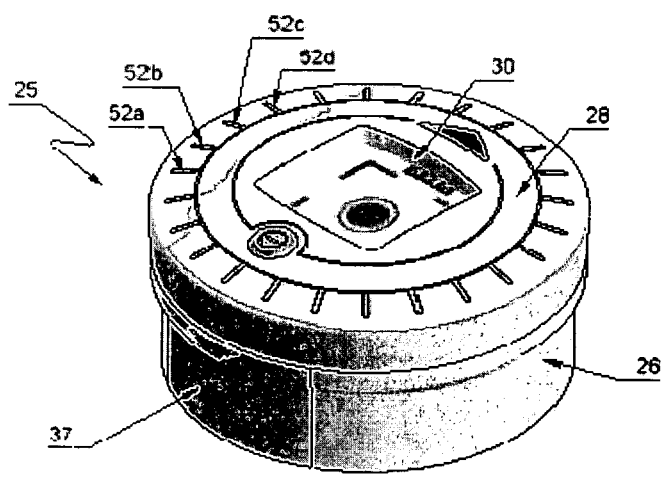
Figure 3:
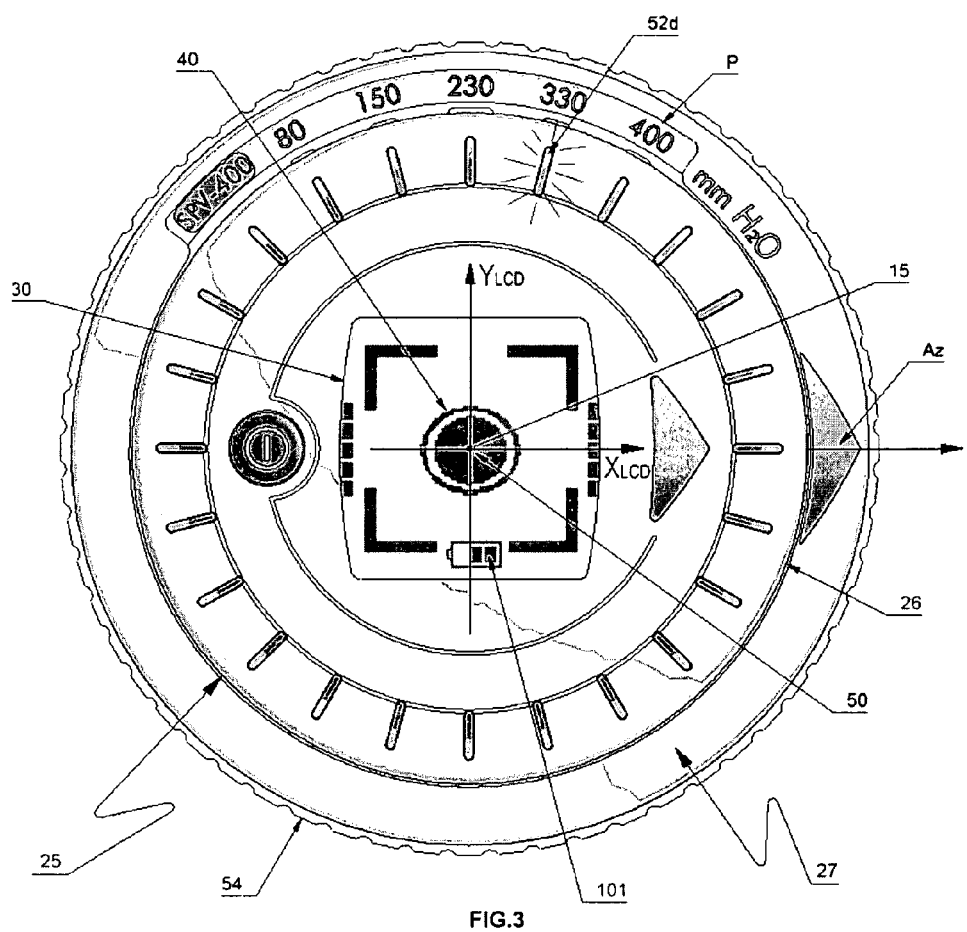
Figure 4:
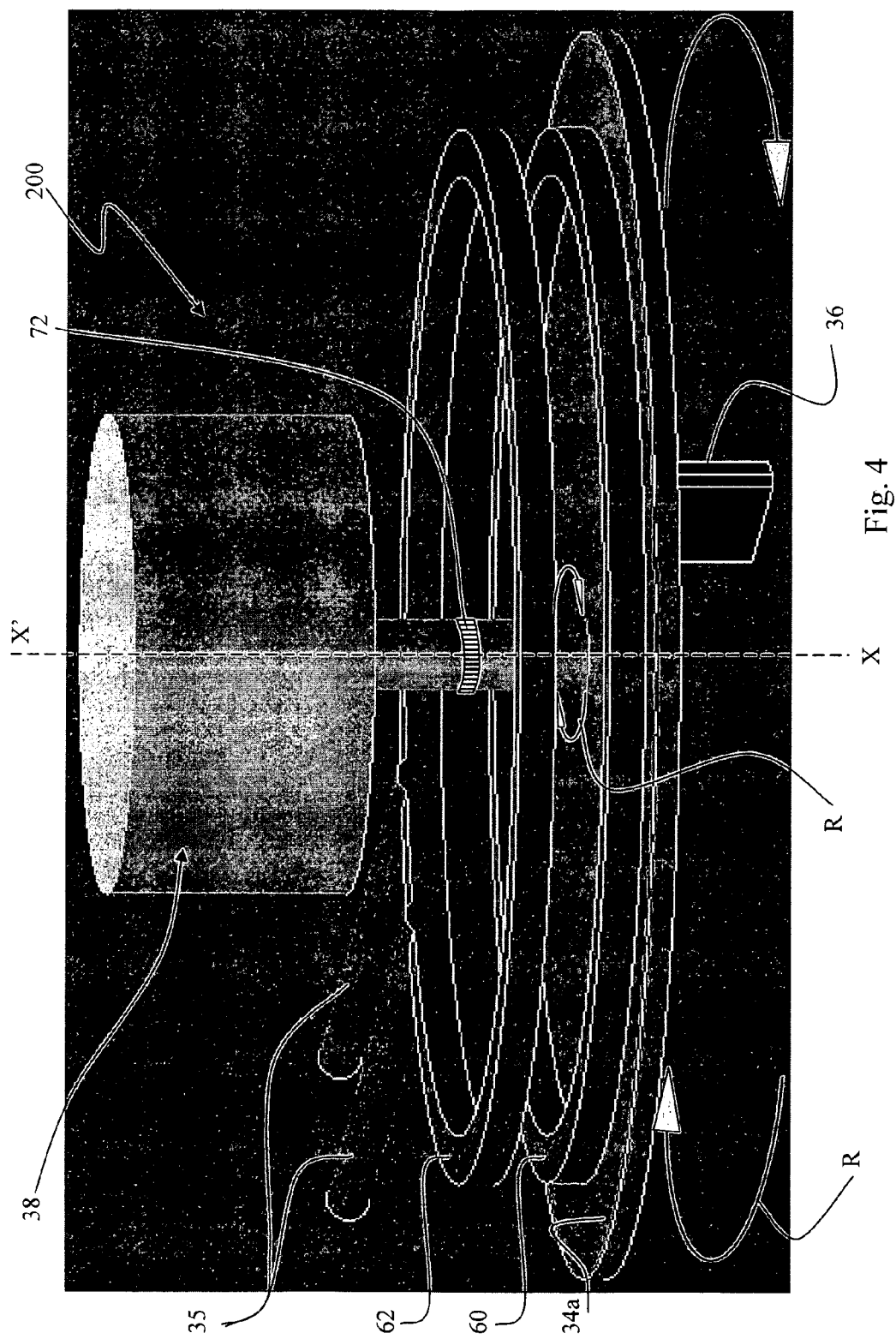
Figure 5:
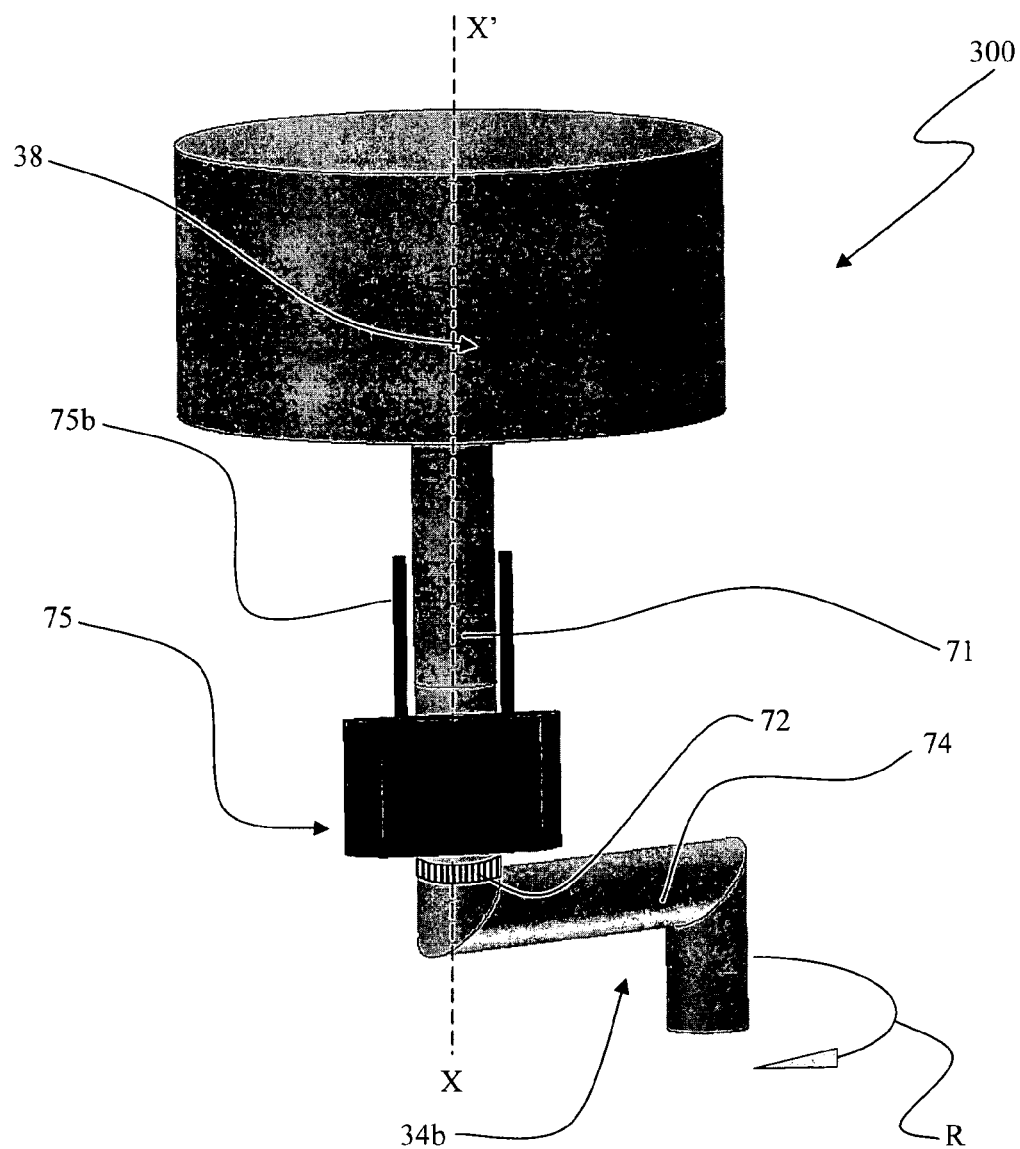
Figure 6:
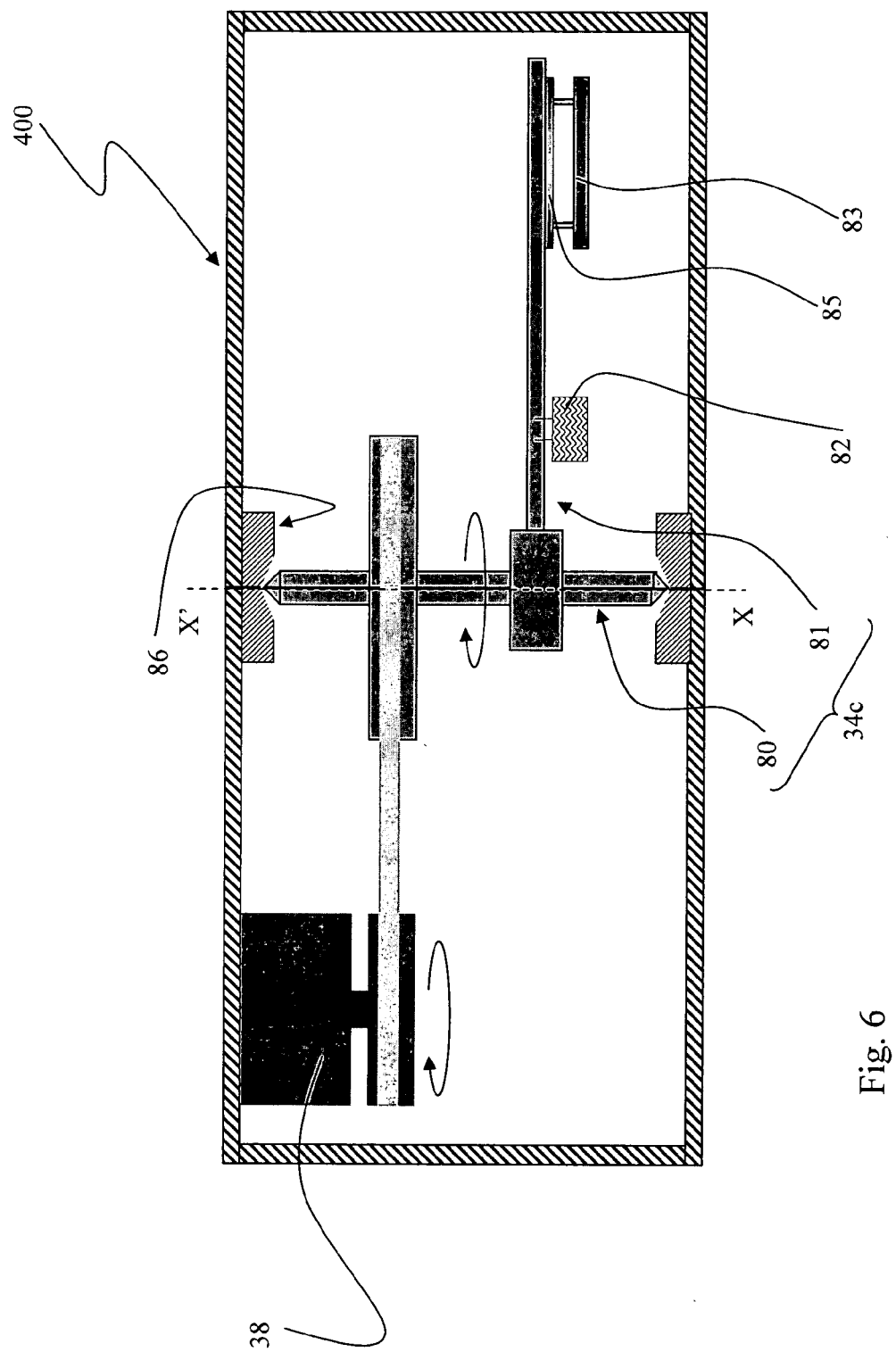
Figure 7:
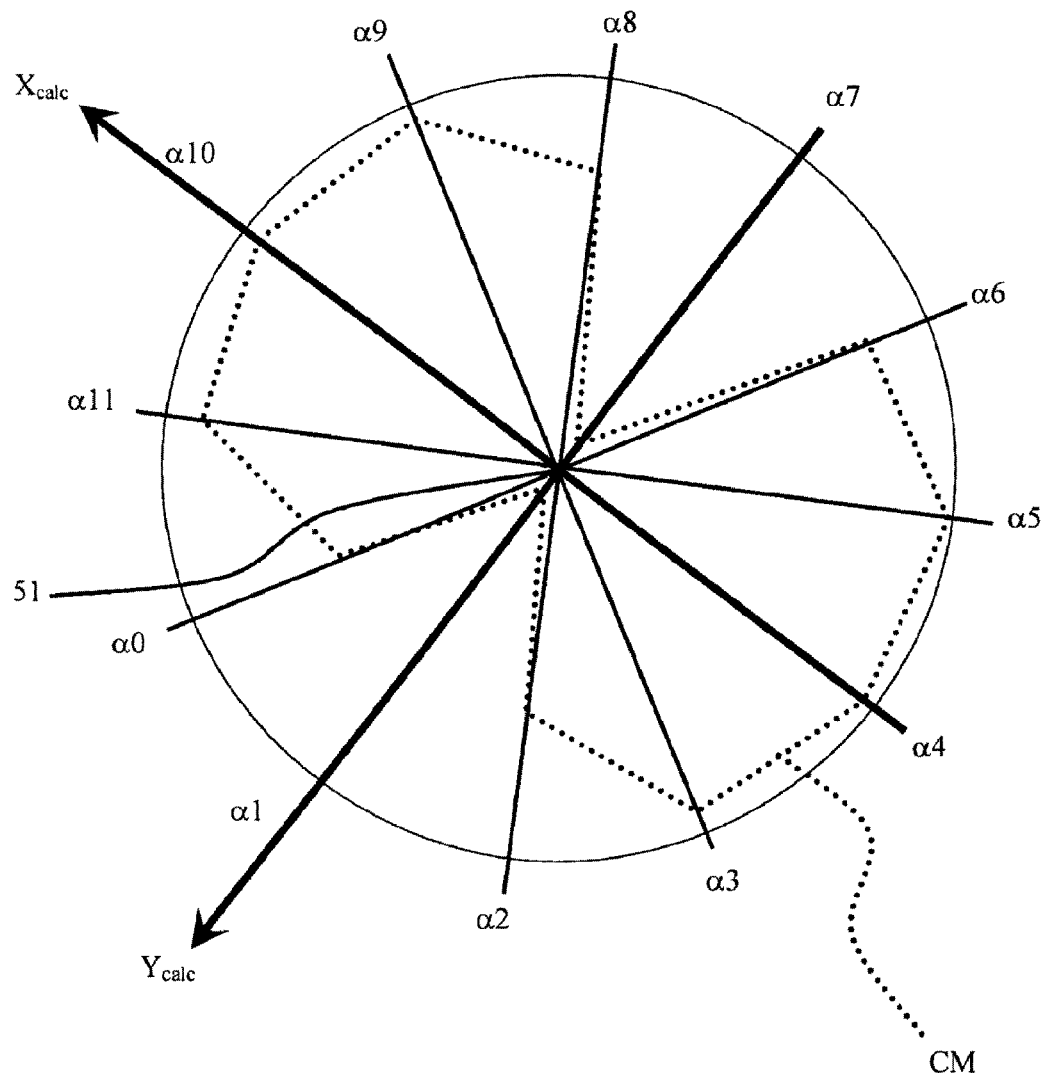
Figure 8:
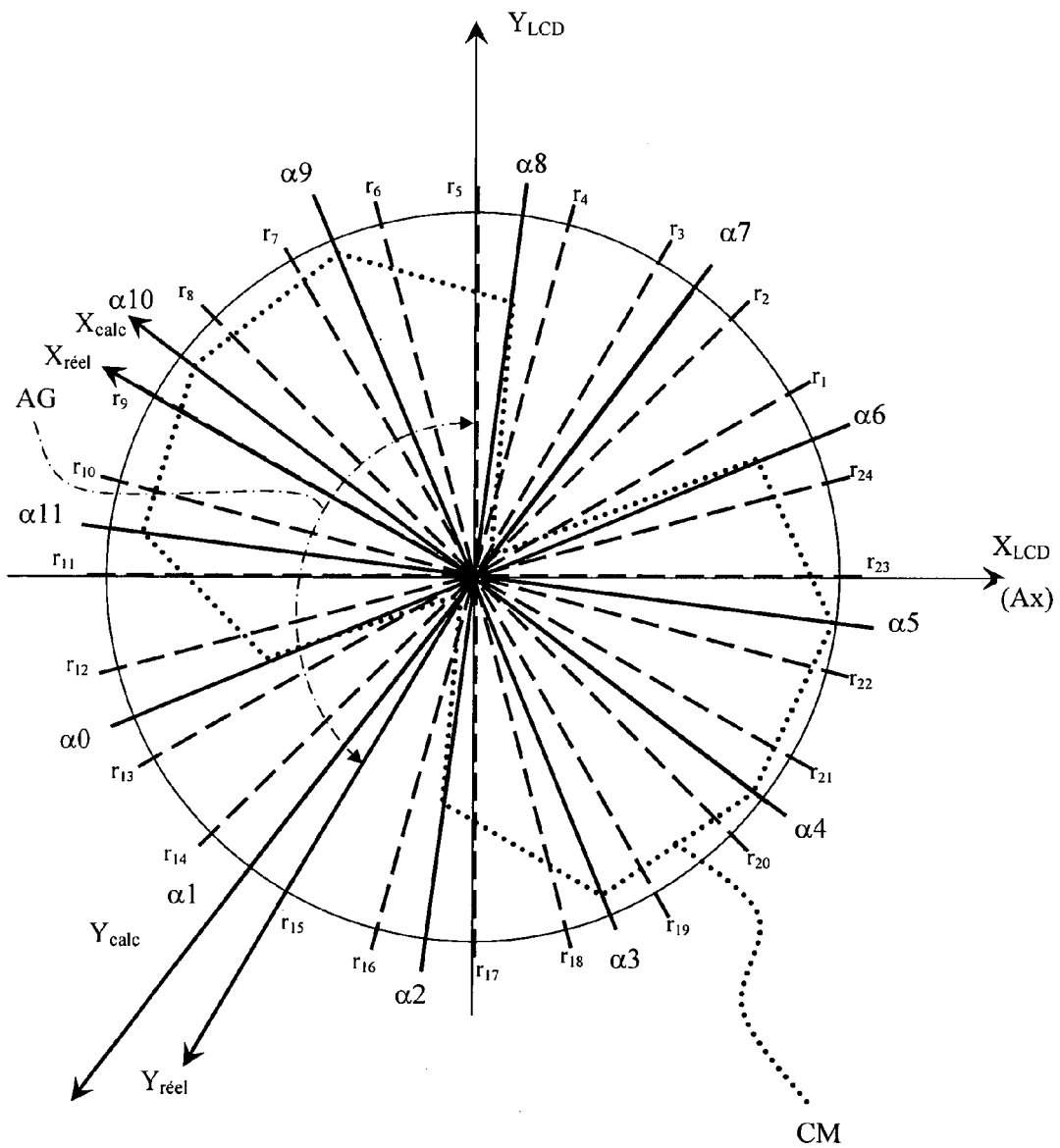

Other characteristics and advantages of the invention will become apparent on reading the detailed description which follows of exemplary embodiments, in conjunction with the appended drawings which represent, respectively:

in FIG. 1, an upper view of an adjustable valve for the treatment of hydrocephalus;

in FIGS. 2a to 2c, upper, lateral sectional and perspective views of an exemplary valve pressure pinpointing and detection device locator according to the invention;

in FIG. 3, an upper, view of a device according to the invention after introducing the above locator into a selector;

in FIG. 4, a front view of a first embodiment of a transponder-based detection and analysis mechanism of a pinpointing and detection device according to the invention;

in FIG. 5, a front view of a second embodiment of a detection and analysis mechanism with bent arm of a pinpointing and detection device according to the invention;

in FIG. 6, a sectional view of a third embodiment of a detection and analysis mechanism with off-centre motor of a pinpointing and detection device according to the invention;

in FIG. 7, a radar chart of measurements of magnetic field of the centre of an implanted valve, carried out with a locator according to the invention; and in FIG. 8, the radar chart of FIG. 7 superimposed on a diagram of the distribution of the setting positions of the valve.

In the whole of the text, the centre of the valve must be understood as the magnetic centre of the valve and not the geometric centre. Additionally, the device according to the invention comprises a magnetic detection source that can consist either of a rotary magnetic sensor, or of a magnetic field conducting rotary piece linked to a fixed sensor, or of a plurality of sensors distributed angularly in a uniform manner.

With reference to FIG. 1, the adjustable valve 10 comprises an input connector 12 and an output connector 14 for fluid, these connectors ensuring the continuity of the flux of the cephalorachidian liquid flowing from a collection catheter to an evacuation catheter. The cephalorachidian liquid (LCR) under pressure may thus be evacuated to the evacuation catheter.

The valve possesses a thermoplastic casing 16 protecting a chamber 18 inside which the LCR flows. The chamber houses two micro magnets, 20 and 22, mounted on a rotor and forming a magnetic dipole 24. The angle AG formed between the direction $X_{real}$ of the dipole 24 and the axis Ax of the connectors 12-14 defines the magnetic orientation of the valve with respect to the axis Ax. This orientation determines the pressure value exerted by the flux of fluid. In order to regulate this pressure, it is appropriate to adjust the angle Ag by rotation about the pivoting axis Ap of the magnetic centre 15 of the valve, to the value corresponding to the pressure desired.

The valve is implanted in the skull of the patient and held in position, for example by stitches.

In order to detect the magnetic centre of the implanted valve and to determine the pressure setting, that is to say the fluid pressure required to allow the valve to open and permit the fluid to flow into this valve, the invention makes provision to implement a locator 25 such as that illustrated in FIGS. 2a to 2c and a selector 27 such as that represented in FIG. 3.

The locator comprises, in a general manner, a casing 26 furnished with a display screen linked to a mechanism for detecting and analysing the magnetic field of the magnetic dipole of the valve.

More precisely, the casing 26 of the locator 25 is cylindrical and comprises an upper face 28 and a bottom face 31. The locator 25 can thus be positioned bearing on the tubular selector 27 and a polarizer device can be disposed on the locator and the selector so that their respective positioning is one-to-one.

The upper face 28 comprises a valve position display screen 30. A central reference sight 40 is indicated on the display screen 30 and a disc 50 corresponding to the position of the magnetic centre of the valve is formed electronically on the screen during the use of the locator by a detection and analysis mechanism situated in the casing 26. Other signals may also be represented by data display indicators, such as the state of charge of batteries 101.

Light-emitting diodes 52a to 52d are disposed on a perimeter of the locator 25, on the upper face 28, to indicate the direction $Y_{real}$ of the dipole of the valve, which information will be utilized to establish the value of the pressure setting of the valve. The diodes may be disposed on a complete or partial perimeter of the casing of the locator. In the exemplary embodiment illustrated in FIGS. 2a, 2c and 3 only the diodes 52a to 52d have been numbered so as not to overload the figure.

The casing 26 comprises, furthermore, buttons for on/off control 58 or for magnetic zeroing 59 (see below).

The casing 26 of the locator 25 contains the detection and analysis mechanism comprising a microprocessor which analyses the measurements of the magnetic field emitted by the micromagnets (20, 22 in FIG. 1) of the dipole 24 of the valve, on the basis of software for analysing the measurements performed by a magnetic detection source.

The casing of the locator also houses accessories: rechargeable batteries or cells 56, an access flap 37, supports 33a, 33b, pillars 33d, casings 39 and connection systems 35 between the various electrical elements, in particular between the battery, the detection and analysis mechanism and the screen (see FIG. 2b). The supports may consist of printed circuits.

The selector 27 exhibits a structure able to house the locator 25. It is of tubular form and exhibits a collar on which is indicated an alignment frame Az for aligning the selector 27 with respect to the axis Ax of flow of the fluid through the valve. This alignment frame Az represents the reference axis of the selector 27 and must be, during use, superimposed on the axis Ax of flow of the fluid through the valve (see below). As represented in FIG. 3, indications of pressure values ranging from 80 to 400 mmH$_2$O are written on the collar 54 of the selector so as to be opposite the diodes 52a to 52d of the locator when the selector 27 and the locator 25 are associated.

The method of analysing the measurements for locating the magnetic centre and determining the setting of the valve will be described later, with reference to FIGS. 7 and 8.

The implementation of the above device is performed as follows, with reference to FIG. 3.

A step of calibrating the locator is performed preferably before any measurement. To do this, the locator must be at a sufficient distance from the valve—about 3 to 4 cm—so as to be outside the magnetic field emitted by the valve. The locator is held in position for a few seconds, the time required to perform a "magnetic zero" measurement by pressing a calibration button, here button 59. The calibration step may also be carried out automatically with a time delay on starting the device. An indicator of auto-calibration with respect to the external magnetic fields may then be activated, but its display during the procedure for searching for the centre and reading the position setting of the valve is optional. Alternatively, the procedure for calibration with respect to the surrounding terrestrial magnetic field is carried out automatically each time the system is turned on. This measurement provides the value of the terrestrial and exterior magnetic fields to be deducted automatically from all the magnetic measurements which will be performed subsequently, during the procedure for searching for the magnetic centre of the valve and for reading the orientation $Y_{real}$ of its dipole 24. The measurements thus will be offset automatically so as to retain only the values specific to the field emitted by the valve. If the magnetic field of the valve is sufficiently large for the influence of the terrestrial magnetic field to be negligible when the locator is situated in proximity to the valve, this zeroing step is not required.

To implement the above device, the alignment frame Az representing the reference axis of the selector 27 is positioned in such a way as to be oriented along the same known direction of the axis Ax of the valve. This direction Ax is determined when implanting the valve and remains constant throughout the life of the patient.

The user then combines the locator 25 with the selector to form the device according to FIG. 3, then activates the locator whose mechanism for detecting and analysing the magnetic field CM of the centre of the valve examines the symmetry of the measured magnetic field, establishes a location signal for the magnetic centre 15 and transmits it to the screen 30 for display in the form of a disc 50. The corresponding method will be explained in greater detail with reference to FIGS. 7 and 8.

In a general manner, the user then displaces the locator 25/selector 27 assembly until the centre of the disc 50 is superimposed on the centre 41 of the sight 40. In this position the magnetic field CM measured is substantially the same, apart from the sign, at substantially diametrically opposite measurement positions. The position of the magnetic centre of the valve is then determined precisely.

There is no need, therefore, to have located the valve by prior palpation in order to locate its magnetic centre since the locator itself indicates the direction to be followed by displaying the magnetic centre of the valve with respect to the sight of the screen. The user therefore knows the direction in which to displace the locator so as to place it accurately above the centre of the valve. Consequently the pinpointing of deeply implanted valves may be performed with the device according to the invention. However, when circumstances lend themselves thereto, and to save time, the user can perform a first location of the valve by palpation in the approximate zone of location of the valve V before aligning the selector with the flow direction Ax.

This precise pinpointing of the magnetic centre by superposition makes it possible to avoid reading errors due to off-centring or parallax in the case of reading with a compass. Moreover, the device can be liberated from the influence of external magnetic fields through a permanent initialization of the offsets of the sensor, until it lies in immediate proximity to the valve, pinpointed by its field of strong intensity.

In a first embodiment illustrated in a general manner in FIG. 2b, the magnetic detection source consists of a magnetic sensor 36 mounted on a support 34 driven in rotation by a motor (not represented) about an axis of rotation (XX').

FIGS. 4 to 6 illustrate three variants of this first embodiment. The locator comprises a mechanism for detecting and analysing the magnetic field of the magnetic dipole of the valve with a revolving sensor. These three variants implement one and the same method for measuring the magnetic field emitted by the valve. The structure of the mechanism differs however from one variant to another.

With reference to FIG. 4, the locator is furnished with a detection mechanism 200 comprising a motor 38 designed to drive in rotation, according to an axis (X-X'), a support 34a comprising a first coil 60 for supplying energy and for transmitting information. The support 34a carries and drives in rotation (arrows R) the coil 60, the magnetic sensor 36 and the microprocessor (not represented) for analysing the measurements and generating detection signals. This first coil 60 is associated with a second fixed coil 62 so as to form an energy transponder for the sensor 36, and to communicate, through the connection systems, the measurements and the data originating from the transponder to the microprocessor. To ascertain the exact angular position of the printed circuit and of the magnetic sensor during rotation, a coded wheel 72 is disposed between the motor 38 and the support 34a.

According to another variant embodiment illustrated in FIG. 5, the locator is furnished with a detection mechanism 300 comprising a motor 38 exhibiting a drive shaft (not visible in the figure), for driving according to an axis of rotation X-X', and linked to a support 34b by a coded wheel 72. In this example, the magnetic support 34b exhibits a doubly bent prolongation 74 made of a magnetic material, in particular ferrite. The prolongation 74 is driven in rotation (arrow R) by the motor and its position is determined by the coded wheel. The magnetic sensor 75 is mounted on a fixed part 71 through which the drive shaft passes, and exhibits two lugs 75b for communicating with a microprocessor (not represented) for analysing the measurements and generating detection signals, which is linked to the display screen.

The piece made of ferrite 74 or some other field-conducting material, constitutes the magnetic detection source. Driven in rotation by the motor, it makes it possible to channel the magnetic field emitted by the magnets of the valve and to transmit it to the fixed magnetic sensor 75. In this case, the measurement of the magnetic field is still performed by a revolving piece which here is linked to a fixed sensor.

According to yet another variant embodiment illustrated in FIG. 6, the locator is furnished with a detection mechanism 400 comprising a motor 38 linked kinematically to a magnetic support 34c, which comprises a central pin 80 and an arm 81 that is fixed to the central pin 80 so as to be driven in rotation with the central pin 80. The arm 81 can consist of a printed circuit equipped with a magnetic sensor 82 and with an information collecting coil 83 associated with a second coil 85 to form an energy transponder for the sensor 82 and to communicate the measurements and data of the sensor 82 to the microprocessor (not represented). The rotary central pin 80 is held rotatably in the casing 26 by energy feed and guide means 86.

The three variant embodiments described above operate as follows.

To locate the magnetic centre of the valve, the user activates the locator, so that the magnetic detection source 36, 74, 82 is rotated about an axis of rotation X-X' in a determined direction of rotation R. The detection source measures the magnetic field emitted by the valve at predetermined angular positions and the microprocessor 32 determines the location of the magnetic centre and displays it in the form of a disc on the screen, as described previously with reference to FIG. 3. Preferably, the magnetic detection source 36, 74, 82 is rotated at a speed of between 600 and 1500 rpm. The user then displaces the locator, that is to say the axis of rotation of the magnetic detection source, until the disc 50 is situated inside the sight 40 represented on the screen 30. Once the disc 50 is inside the sight 40 the device displays the position setting of the valve.

An exemplary method for determining the magnetic centre is described hereinbelow with reference to FIGS. 7 and 8.

After having calibrated the sensor according to the surrounding magnetic field, the device loops through the following general algorithm:
- calculation of the position setting (with no display of said position);
- search for the magnetic centre;
- display of the centre, in the form of a disc;
- display of the position setting, when the disc is inside the sight, and possibly display of the depth of the valve.

After alignment of the axis $X_{LCD}$ of the screen 30 of the locator and the axis Ax of the valve, the software for analysing the magnetic measurements determines the orientation of the valve, by determination of the orientation of the axis $X_{real}$ of the magnetic dipole with respect to the known direction of the axis Ax.

The measurements of the magnetic field sensed by the magnetic detection source 36, 74, 82 must be carried out in sufficient number $n_a$ per revolution to calculate, by comparing measurements, the position of the centre of the valve and then the orientation of its magnetic dipole, once the locator is placed on the centre of the valve, the orientation of the dipole determining the setting of the valve. For example, a number $n_a$ chosen equal to 12 measurements per revolution (FIG. 7), that is to say every 30 degrees, leads to reliable results for a valve exhibiting position settings spaced 15 degrees apart. In other examples, 24, or even 36 measurements may be performed during a revolution if the position settings are spaced 7.5 degrees and 5 degrees apart respectively. These measurement positions are spaced uniformly apart and should not be grouped into sub-groups, or the measurements will be corrupted. In a general manner, $n_a$ will be chosen so that $360/n_a = 2*A_R$ where $A_R$ is the angle between two position settings of the valve. The angle between two measurement positions is therefore equal to $360/n_a$.

An example of the method is given for determining the setting of a SOPHYSA valve referenced "Polaris SPV", hereinbelow denoted "Sophysa valve", having a number of position settings $n_R$ equal to twenty-four (numbered from $r_1$ to $r_{24}$), the position settings being separated by an angle $A_R$ of 15°. In this valve, the position $r_5$ is aligned with the axis $Y_{LCD}$ of the screen of the locator which is at 90° to the axis $X_{LCD}$ (see FIG. 8) when the locator is placed on the centre of the valve.

The detector used comprises twelve measurement positions, that is to say, the analysis is done on a series of measurements taken at twelve positions of the sensor during a revolution ($n_a=12$).

The measurement positions are numbered from $\alpha 0$ to $\alpha 11$ in a manner which increases with the direction of rotation R of the sensor. In the embodiment illustrated in FIG. 7 the numbering direction has been chosen by convention as being the trigonometric direction of rotation (anticlockwise). The measurement position numbered $\alpha 0$ depends on the valve. For the Sophysa valve, the position $\alpha 0$ is the sensor position situated between the position settings $r_{12}$ and $r_{13}$ (see FIG. 8). For another valve, the measurement position $\alpha 0$ could correspond to a different position.

In the configuration illustrated in FIG. 8, the magnetic field detection positions are chosen so as to be offset angularly with respect to the position settings so that two position settings are distributed regularly between two successive detection positions. In the configuration with twelve detection positions and twenty-four position settings, a first detection position is separated from a first position setting by an angle of 7.5°, itself separated from a second position setting by an angle of 15°, itself separated from a second detection position by an angle of 7.5°.

The measurements are recorded and allocated a sign + or − depending on whether the magnetic field measured is positive or negative. Thus, in the example of FIG. 7, the measurement positions $\alpha 2$ to $\alpha 7$ correspond to negative values of the magnetic field. However, in a conventional manner, the radar image of FIG. 7 is obtained with the aid of these absolute value measurements.

The first step of the method consists in searching for the measurement position corresponding to a negative signal exhibiting the largest absolute value, here $\alpha 5$. Let Imax1 be the number for this position; Imax1=5. This position is taken as starting point for the rest of the analysis which is performed in the direction in which the sensor position numbers increase, that is to say in the direction of rotation of the sensor.

The second step consists in searching, among the subsequent measurement positions, for the one having the strongest positive signal, here $\alpha 9$. Let Imax2 be the number for this position; Imax2=9. In the case of a significant off-centring of the radar image, the search for Imax2 may involve a restricted number of measurement positions after the position Imax1. This restricted number may be equal to $(n_a/2)+2$. In the example of FIG. 7, the search can involve only the eight (12/2+2) measurement positions following Imax1.

The third step consists in searching, in the direction of rotation of the sensor, between Imax1 and Imax2 (not between Imax2 and Imax1), for the measurement position having the weakest signal in absolute value, here α7 (and not α1). Let Imin1 be the number for this position; Imin1=7.

The fourth step consists in searching, among the measurement position preceding the position whose number is Imin1 and the position following the latter position, for the position having the weakest signal in absolute value: here α8. Let Imin2 be the number for this position; Imin2=8.

The position setting for the valve with twenty-four positions, corresponding to the orientation of the axis $Y_{real}$ of the magnetic dipole with respect to the axis Ax, is then:
either Imin1+Imin2, if Imin1 precedes Imin2,
or Imin1+Imin2+1, if Imin2 precedes Imin1.

In the example illustrated, α7 precedes α8, hence the position setting of the valve is 7+8=15. This signifies that the axis $Y_{real}$ coincides with the position setting $r_{15}$.

In the extreme cases where Imin1=11 and Imin2=0, the number for the pressure setting is 23. Conversely, when Imin1=0 and Imin2=11, then the number for the pressure setting is 24.

The axis $Y_{real}$ is oriented in the direction of this position setting. In the example illustrated in FIG. 8, $Y_{real}$ is oriented towards the position setting $r_{15}$.

After having determined the position setting of the valve, the locator according to the invention searches for the magnetic centre of the valve and displays it on the screen of the locator so that the user can accurately align the locator above the centre of the valve.

The search for the magnetic centre is performed in the following manner. The processing is done on the twelve values arising from the twelve measurement positions numbered from α0 to α11.

The objective is to determine an orthonormal calculation frame defined by an axis $X_{calc}$ and an axis $Y_{calc}$, for calculating the coordinates Xc and Yc of the magnetic centre in the frame $(X_{real}, Y_{real})$. Thereafter, these coordinates are referred to in the orthonormal frame $(X_{LCD}, Y_{LCD})$ of the locator.

The orthonormal calculation frame is determined as follows:
$Y_{calc}$, the axis passing through the measurement positions corresponding to the weakest signals in absolute value. In the example illustrated in FIG. 8, $Y_{calc}$ passes through the measurement positions α7 and α1. By convention, $Y_{calc}$ is oriented in the direction of α1 which is the measurement position nearest to the position setting $r_{15}$ (see FIG. 8);
$X_{calc}$, the axis perpendicular to $Y_{calc}$. In the example illustrated in FIG. 8, $X_{calc}$ passes through the measurement positions α10 and α4. By convention, $X_{calc}$ is here oriented in the direction of α4.

The lobes of the radar image of FIG. 7 are therefore distributed on either side of the axes $X_{calc}, Y_{calc}$ and $X_{real}, Y_{real}$. This distribution depends, on the one hand, on the position of the locator with respect to the centre of the valve and, on the other hand, on the offset between $Y_{calc}$ and $Y_{real}$. This offset is a maximum of 7.5°, having regard to the distribution adopted for the measurement positions and position settings.

To characterize the distribution of these lobes on either side of the axes $X_{real}$ and $Y_{real}$, the values of the magnetic field detected are separated, in the frame $(X_{calc}, Y_{calc})$, into two groups.

To do this, the number for the position setting ("POS") is used to determine a measurement position "START" as follows:
if "POS" is greater than or equal to 5, then "START"= ("POS"−5)/2
else "START"=("POS"+19)/2.

The value 5 corresponds to the position setting $r_5$ which, as will be recalled, is aligned with the axis $Y_{LCD}$ of the screen of the locator. The value 19 corresponds to the number of position settings (twenty-four) minus the position aligned with the axis $Y_{LCD}$ of the locator (five).

In a more general manner, if the position setting $r_i$ is aligned with the axis $Y_{LCD}$ of the locator, the reference measurement position "START" is determined as follows:
if "POS" is greater than or equal to i, then "START"= ("POS"−i)/2
else "START"=("POS"+$(n_R$−i))/2.

If the calculation of START culminates in a non-integer value, the value of START is the integer part of the non-integer value calculated.

In the example illustrated in FIG. 8, the reference measurement position "START" is the position α5 (that is to say (15−5)/2).

By virtue thereof, the twelve measurement positions are separated, in the frame $(X_{calc}, Y_{calc})$, into two groups of six $(n_a/2)$ values:
the first group consists of the six measurement positions in the direction in which the numbers increase from "START" (inclusive),
the second group consists of the other six measurement positions.

In FIG. 8, the first group consists of the six measurement positions α5, α6, α7, α8, α9 and α10. The second group consists of the six measurement positions α11, α0, α1, α2, α3 and α4.

The calculation of the coordinates of the magnetic centre is performed as follows:
Xc is equal to the sum of the three positive maximum values minus the absolute value of the sum of the three negative maximum values. Xc represents the degree of symmetry of the lobes on either side of the axis $Y_{real}$. Stated otherwise, when Xc is substantially equal to zero, the lobes are substantially symmetric with respect to the axis $Y_{real}$.
In FIG. 8, the three positive maximum values are given by the measurement positions α9, α10 and α11, and the three negative maximum values are given by the measurement positions α3, α4 and α5.
Yc is equal to the sum of the absolute values of the three maximum values of the first group minus the sum of the absolute values of the three maximum values of the second group. Yc represents the degree of symmetry of the lobes on either side of the axis $X_{real}$. Stated otherwise, when Yc is substantially equal to zero, the lobes are substantially symmetric with respect to the axis $X_{real}$.
In FIG. 8, the three maximum values of the first group are given by the measurement positions α5, α9 and α10, and the three negative maximum values are given by the measurement positions α11, α3 and α4.

To help the user to displace the locator in such a way that the magnetic centre is placed at the centre 41 of the sight 40 of the screen 30, the invention makes provision to display in the display frame $(X_{LCD}, Y_{LCD})$ a disc with coordinates (Xc, Yc) of the magnetic centre 15, which are calculated in the frame $(X_{real}, Y_{real})$ determined by the position setting.

Of course, the centre 41 of the sight 40 is the origin of the frame ($X_{LCD}$, $Y_{LCD}$). It is therefore necessary to perform a change of frame.

Thus, this involves performing a rotation of angle "AG" since the axes Ax and $X_{LCD}$ coincide and the axes $X_{LCD}$ and $Y_{LCD}$ are perpendicular.

Hence, AG=−15*("POS"−5), "AG" here being expressed in degrees. The value 15 is the number of degrees between two measurement positions. The value 5 corresponds to the position setting $r_5$ aligned with the axis $Y_{LCD}$ of the locator. More generally, AG=$A_R$×(POS−i), where i is the number for the position setting $r_i$ aligned with the axis $Y_{LCD}$.

The following are finally obtained:

$$Xaff = Xc \cdot \cos(AG) - Yc \cdot \sin(AG)$$

$$Yaff = Xc \cdot \sin(AG) + Yc \cdot \cos(AG)$$

The detection and analysis mechanism then transmits the coordinates Xaff and Yaff to the screen for display in the form of a disc in the frame ($X_{LCD}$, $Y_{LCD}$).

The user therefore merely has to displace the locator, while keeping the alignment frame Az oriented along the same known direction of the axis Ax of the valve, until the disc lies in the sight. The above method therefore amounts to displacing the magnetic detection source until the lobes of the magnetic field are substantially symmetric with respect to the axes $X_{real}$ and $Y_{real}$. When the magnetic centre is placed at the centre of the sight, Xaff=0 and Yaff=0.

In this situation, the locator recalculates and then displays the position setting. Preferably, the locator can emit a luminous and/or audible signal.

The pinpointing of the orientation of the dipole 24, or calculation of the position setting, is useful for displaying on the screen 30 of the locator the position of the magnetic centre of the valve. It is therefore understood that the calculation of the position setting is not an indispensable prior step for determining the position of the magnetic centre. If this step is omitted, it suffices to adopt a convention of separation, in the frame ($X_{calc}$, $Y_{calc}$), of the $n_a$ measurement positions into two groups of $n_a/2$ positions to calculate Yc. For example, it is possible to choose that if $Y_{calc}$ passes and is oriented towards the position αi, then "START"=i+(($n_a/4$)+1). In the example described above, START would be calculated as follows: 1+((12/4)+1)=5 since $Y_{calc}$ passes and is oriented towards the position α1. The first group is then made up of the $n_a/2$ positions following START inclusive and the second group is made up of the $n_a/2$ other positions. The angle of rotation for display in the frame ($X_{LCD}$, $Y_{LCD}$) would then be done between $Y_{calc}$ and $Y_{LCD}$.

By way of example, the sight may exhibit a radius of 1 mm to 2 mm, depending on the accuracy required.

Thus, when the magnetic centre 15 (FIG. 1) of the valve is pinpointed and the reference axes of the locator 25 and of the valve 10 are aligned (respectively Az and Ax), the determination of the position setting of the valve makes it possible to light up the light-emitting diode (52*d* on FIG. 3) corresponding to the pressure value displayed on the collar 54 of the selector 27. In the example illustrated in FIG. 3, P=330 mm $H_2O$ (i.e. around 3235 Pa), on the annular collar 54 opposite the lit diode 52*d* and/or on an additional optional indicator (not represented).

According to another aspect of the invention, the locating device according to the present invention also makes it possible to ascertain whether the depth of implantation of the valve is less than a recommended maximum depth, beyond which it is no longer possible to unlock the magnetic rotor and to modify its angular position with the help of an adjustment magnet.

Thus, in a preferred embodiment, the locator calculates the depth of implantation of the valve on the basis of the mean of the absolute values of the measurements taken at each position $\alpha_n$, and indicates the depth of the valve by comparing the mean obtained with predetermined calibration values.

Such an indication may be made, for example, by making the intensity of coloration of the disc 50 vary, going from white to black, as a function of the depth of the valve under the skin, in particular when the centre of the sight is superimposed with the centre of the disc. Under these conditions, a device according to the invention advantageously makes it possible to establish, as a function of the intensity of its coloration, whether the depth of implantation of the valve remains less than or at most equal to the predetermined threshold value.

According to another variant, the depth of the valve 10 can be displayed directly on the screen 30, independently of the valve pinpointing signal, by a numerical indicator or a bar graph 103.

In a second embodiment of the invention, the device according to the invention comprises a magnetic detection source comprising a plurality of sensors angularly distributed in a uniform manner at predetermined angular positions (for example from $\alpha_1$ to $\alpha_{12}$). This distribution corresponds to the measurement positions of the revolving sensor of the first embodiment described above. The minimum number of sensors also depends on the angular offset between two position settings and the implementation of this second embodiment is identical to the first.

The other characteristics described in respect of the first embodiment with a rotary sensor are adaptable to the second embodiment with the plurality of sensors.

For example, the locator comprises a casing furnished with a mechanism for detecting and analysing the magnetic field of the magnetic dipole of the valve comprising the magnetic detection source furnished with the plurality of sensors angularly distributed in a uniform manner at predetermined angular positions around an axis of symmetry, linked to a microprocessor for analysing the measurements and generating detection signals and to a valve position display screen.

The above method may be adapted to any valve locator exhibiting position settings spaced apart by a determined angle. The number of measurement positions or sensors is determined by this angle separating two position settings. Additionally, the numbering of the first detection position or of the first sensor α0 depends on the position settings of the valve and their alignment with respect to the display frame ($X_{LCD}$, $Y_{LCD}$) or to the direction of flow of the fluid (Ax or $X_{LCD}$). The numerical relation determining the position setting on the basis of Imin1 and Imin2 may also be adapted, for example by adding or deducting a constant, to obtain the corresponding position setting number for the valve. Thus, in practice, the locator according to the invention can be adapted easily to any type of valve.

The invention is not limited to the exemplary embodiments described and represented. The structure of the device can be in two parts, selector and locator, or in one single part. In the latter case a collar of the type described above is fixed around the perimeter of the locator.

Additionally, the magnetic sensor can, for example, be a magnetorestrictive, inductive, piezoelectric or Hall-effect sensor.

It is also possible to dispose several sensors on the axis prolonged by at least one arm that is bent during rotation, or to dispose several sensors regularly distributed over the revolving coil of the transponder.

According to other embodiments, at least one sensor, respectively fixed or revolving, is associated with any element, respectively revolving or fixed, of suitable form (continuous or discontinuous, axisymmetric or cylindrical with appropriate cross section) adapted to the channelling of the magnetic field emitted by the valve.

Additionally, the locating signal for the magnetic centre of the valve is not necessarily depicted in the form of a disc. Its representation may evolve as a function of its distance with respect to the sight and in particular go from an arc to a circle or from an angular sector to a disc when the locator is situated precisely above the centre of the valve.

The invention claimed is:

1. A method for electronically locating a magnetic center of an implanted magnetic adjustable valve exhibiting a fluid flow reference axis (Ax) and a center furnished with a magnetic dipole (24), wherein said method comprises of the following steps:
    pinpointing the fluid flow reference axis (Ax) for flow of fluid through the valve (10),
    activating a mechanism for electronically detecting a magnetic field (36, 74, 82) at predetermined measurement positions ($\alpha_1$-$\alpha_{12}$) angularly and uniformly distributed in a circle around an axis (X-X'),
    electronically measuring the magnetic field (CM) emitted by the valve at the predetermined measurement positions ($\alpha_1$-$\alpha_{12}$),
    displacing the mechanism for electronically detecting a magnetic field until the magnetic field measured is substantially the same at substantially diametrically opposite positions, the magnetic center of the valve being in the center between said opposite positions.

2. The locating method according to claim 1, furthermore comprising the step of pinpointing an orientation of the dipole (24) of the valve with respect to the flow axis (Ax) on the basis of the magnetic field measurements, the orientation of the dipole determining a setting of the valve.

3. The locating method according to claim 2, in which the orientation of the dipole is pinpointed by implementing the following steps:
    a) searching for a measurement position Imax1 having a strongest negative signal;
    b) searching, on the basis of the position Imax1 determined in step a) and according to a direction of rotation of the mechanism, among the subsequent measurement positions, for a position Imax2 having a strongest positive signal;
    c) searching for a measurement position Imin1 of a sensor having a weakest signal in terms of absolute value situated between the two positions Imax1 and Imax2 determined in steps a) and b);
    d) determining, from among the measurement positions preceding and succeeding the position Imin1 determined in step c), the position Imin2 of the sensor having the weakest signal in terms of absolute value;
    a setting position of the valve being equal to: Imin1+Imin2, if Imin1 is less than Imin2, or to Imin1+Imin2+1, if Imin2 is less than Imin1.

4. The locating method according to claim 1, comprising, furthermore, the steps of calculating a depth of implantation of the valve on the basis of a mean of the absolute values of the measurements taken at each position, and of indicating the depth of the valve by comparing the mean obtained with predetermined calibration values.

5. The locating method according to claim 1, in which the mechanism for electronically detecting a magnetic field (36, 74, 82) is rotated about said axis (X-X') and in a determined direction of rotation (R), the measurements of the magnetic field (CM) emitted by the valve being made at the predetermined measurement positions ($\alpha_1$-$\alpha_{12}$).

6. The locating method according to claim 5, in which the mechanism for electronically detecting a magnetic field (36) moves in rotation at constant speed during the measurements.

7. The locating method according to claim 6, in which the mechanism for electronically detecting a magnetic field (36) is associated with a magnetic field channelling means.

8. The locating method according to claim 1, in which the mechanism for electronically detecting a magnetic field comprises a plurality of sensors angularly distributed in a uniform manner at predetermined measurement positions ($\alpha_1$-$\alpha_{12}$) around said axis (X-X'), the measurements of the magnetic field (CM) emitted by the valve being made by each sensor of the mechanism for electronically detecting a magnetic field at the predetermined measurement positions ($\alpha_1$-$\alpha_{12}$).

9. A locator of a magnetic center of an implanted valve with a center furnished with a magnetic dipole the locator comprising:
    a mechanism for electronically detecting and measuring a magnetic field (CM) of the magnetic center (15) of the valve at predetermined measurement positions ($\alpha_1$-$\alpha_{12}$) angularly and uniformly distributed in a circle around an axis (X-X'), linked to
    a microprocessor (32) for analyzing the magnetic field measurements and for generating detection signals, and
    a casing (26) surrounding the mechanism and the microprocessor.

10. The locator according to claim 9, in which there is provided a screen (30) for displaying a position of the magnetic center of the valve.

11. The locator according to claim 10, in which the detection signals generated by the microprocessor (32) are embodied by a visual signal on the screen (30) or an audible signal.

12. The locator according to claim 11, in which the visual signal is constant or varies as a function of a distance between the valve (10) and the locator (25), wherein the location of the magnetic center of the valve is acquired when a disc (50) is centered in a sight (40).

13. The locator according to claim 10, comprising an indicator for displaying a depth of the valve (10) independent of a valve pinpointing signal.

14. The locator according to claim 13, wherein the indicator is a bar graph (103).

15. The locator according to claim 9, in which the mechanism for electronically detecting a magnetic field (36, 74, 82) is mounted rotatably about said axis (X-X') and a direction of rotation (R).

16. The locator according to claim 15, in which the mechanism for electronically detecting a magnetic field comprises at least one magnetic sensor (36) for performing the measurements of magnetic field of the magnetic center of the valve and a support (34, 34a, 34b) able to be driven in rotation by a motor (38).

17. The locator according to claim 9, in which the mechanism (200) for detecting the magnetic field of the magnetic dipole of the valve comprises a motor (38) configured to drive in rotation, according to said axis (X-X'), a support (34a) comprising a first coil (60) for supplying energy and transmitting information and a magnetic sensor (36), the first coil (60) being associated with a second fixed coil (62) to form an energy transponder for the sensor (36) and to communicate the measurements and the data originating from the transponder to the microprocessor (32), a coded wheel (72) being disposed between the motor (38) and the support (34*a*) for ascertaining an exact angular position of the magnetic sensor during rotation.

18. The locator according to claim 9, in which the mechanism (300) for detecting the magnetic field of the magnetic dipole of the valve comprises a motor (38) exhibiting a shaft for driving according to said axis (X-X'), covered by a fixed hood (71) on which is positioned a magnetic sensor (36), able to communicate with said microprocessor (32), and linked kinematically to a support (34*b*) by a coded wheel (72), the support (34*b*) exhibiting a doubly bent prolongation (74) made of a magnetic material whose position is determined by the coded wheel (72).

19. The locator according to claim 9, in which the mechanism (400) for detecting the magnetic field of the magnetic dipole of the valve comprises a drive motor (38) kinematically linked to a support (34*c*) comprising a rotary central pin (80) linked kinematically to the drive motor (38) and an arm (81) fixed to the central pin (80) so as to be driven in rotation with the central pin (80), the arm (81) being equipped with a magnetic sensor (82) and with an information collecting coil (83) associated with a second coil (85) to form an energy transponder for the sensor (82) and to communicate the measurements and the data of the sensor (82) to the microprocessor (32).

20. The locator according to claim 9, in which the mechanism for electronically detecting a magnetic field comprises a plurality of sensors angularly distributed in a uniform manner at predetermined measurement positions ($\alpha_1$-$\alpha_{12}$) around the axis (X-X').

21. The locator according to claim 9, in which light-emitting diodes (52*a*-52*d*) are disposed around a perimeter of the casing (26) of the locator and are linked to the microprocessor (32) for analyzing the magnetic field measurements, wherein a diode corresponding most closely to an orientation of the magnetic dipole (24) of the valve lights up, and a pressure (P) corresponding to the orientation can be read in regard to the lit diode when the magnetic center (15) is located and reference axes of the locator (Az) and the valve (Ax) are aligned.

22. The locator according to claim 9, comprising a sound emitter able to emit a particular sound signal when positions of the magnetic center (15) of the valve (10) and of a sight (41) of the locator (25) are superimposed.

23. The locator according to claim 9, in which the mechanism for electronically detecting a magnetic field (36) is a magnetorestrictive, inductive, piezoelectric or Hall-effect sensor.

24. A device for pinpointing and detecting valve pressure of a valve with a magnetic center furnished with a magnetic dipole the device comprising:
 a locator comprising a casing (26), wherein said casing surrounds:
 a mechanism for electronically detecting and measuring a magnetic field (CM) of the magnetic center (15) of the valve at predetermined measurement positions ($\alpha_1$-$\alpha_{12}$) angularly and uniformly distributed in a circle around an axis (X-X'), linked to
 a microprocessor (32) for analyzing the magnetic field measurements and for generating detection signals and a selector (27) of tubular structure exhibiting a collar (54) configured as a seat for the locator (25), the collar (54) comprising an alignment frame (Az) for aligning the selector with respect to an axis (Ax) of flow of the fluid through the valve (10);
wherein said locator and said selector are two separable units.

25. The device according to claim 24, wherein light-emitting diodes (52*a*-52*d*) are disposed around a perimeter of the casing (26) of the locator and are linked to the microprocessor (32) for analyzing the magnetic field measurements, wherein a diode corresponding most closely to an orientation of the magnetic dipole (24) of the valve lights up, and a pressure (P) corresponding to the orientation can be read in regard to the lit diode when the magnetic center (15) is located and reference axes of the locator (Az) and the valve (Ax) are aligned and wherein the collar (54) carries indications of pressure values written to be opposite the diodes (52*a*-52*d*) of the locator when the selector (27) and the locator (25) are associated.

* * * * *